United States Patent [19]

Bauer

[11] Patent Number: 5,361,782

[45] Date of Patent: Nov. 8, 1994

[54] INTRANASAL SEPTAL STAPLING METHOD

[76] Inventor: William Bauer, 80 Summerhill Pl., Newnan, Ga. 30263

[21] Appl. No.: 79,272

[22] Filed: Jun. 21, 1993

Related U.S. Application Data

[62] Division of Ser. No. 858,028, Mar. 26, 1992.

[51] Int. Cl.$^5$ ............................................. A61B 17/00
[52] U.S. Cl. .................................. 128/898; 606/196; 606/219
[58] Field of Search .............................. 128/897–898; 606/219–220, 215–216, 228–230, 196

[56] References Cited

U.S. PATENT DOCUMENTS

| | | |
|---|---|---|
| D. 279,501 | 7/1985 | Sprekelmeier . |
| D. 301,740 | 6/1989 | Green . |
| 661,598 | 11/1900 | Callison . |
| 2,853,074 | 9/1958 | Olson . |
| 3,082,426 | 3/1963 | Miles . |
| 3,278,107 | 10/1966 | Rygg . |
| 3,470,875 | 10/1969 | Johnson . |
| 3,575,038 | 4/1971 | Mallett . |
| 3,935,859 | 2/1976 | Doyle ............................ 606/199 X |
| 4,031,569 | 6/1977 | Jacob ............................. 606/199 X |
| 4,402,314 | 9/1983 | Goode ............................ 606/199 X |
| 4,615,474 | 10/1986 | Strekopytov . |
| 4,633,861 | 1/1987 | Chow . |
| 4,664,305 | 5/1987 | Blake, III et al. ............. 606/219 X |
| 4,938,763 | 7/1990 | Dunn et al. ..................... 604/891.1 |
| 4,991,764 | 2/1991 | Mericle . |
| 5,125,553 | 6/1992 | Oddsen . |

Primary Examiner—Angela D. Sykes
Attorney, Agent, or Firm—Cushman, Darby & Cushman

[57] ABSTRACT

A stapling device is provided including first and second arms, each arm having a distal portion, a central portion and proximal portion; a stapler head rotatably coupled to a free end of the distal portion of the second arm. The stapler head has a first, inoperative position and a second operative position. The device includes a member for moving the stapler head from the inoperative position to the operative position, and elements for pivotly coupling the central portion of the first arm to the central portion of the second arm. The stapling device further includes first and second handle elements each pivotly coupled to each other and to the proximal portions of the first and second arms and operatively coupled to the moving member so that initial displacement of the handle elements from an inoperative position towards each other moves the distal portions of the first and second arms towards each other and actuates the moving member to move the stapler head from the inoperative position to the operative position. Further displacement of the handle elements displaces the second arm to bring the stapler head and the first arm into contact with tissue structure to be stapled. Release of the handle elements allows the moving member to return the stapler head to the inoperative position. A method for employing the stapling device is also provided.

4 Claims, 5 Drawing Sheets

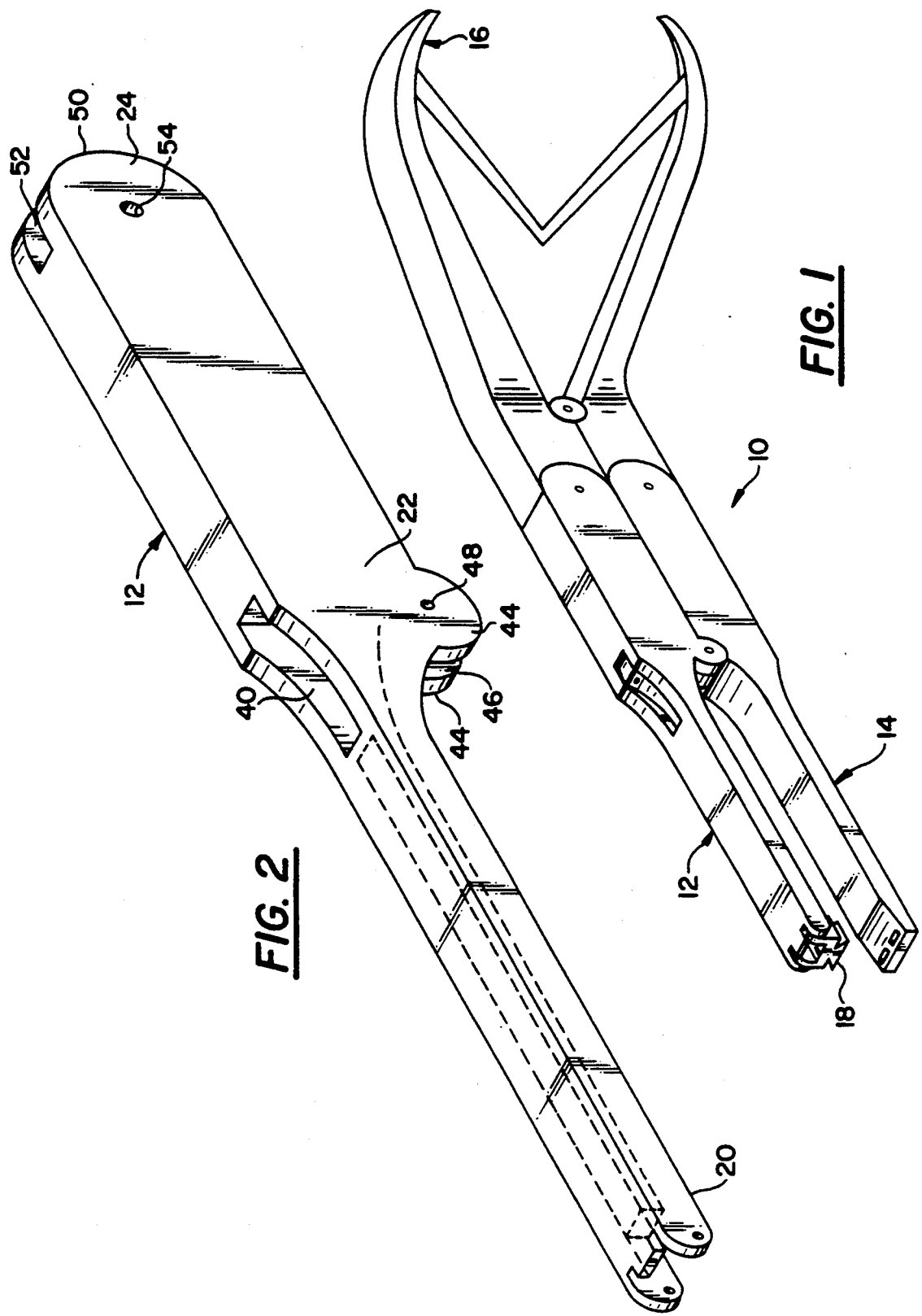

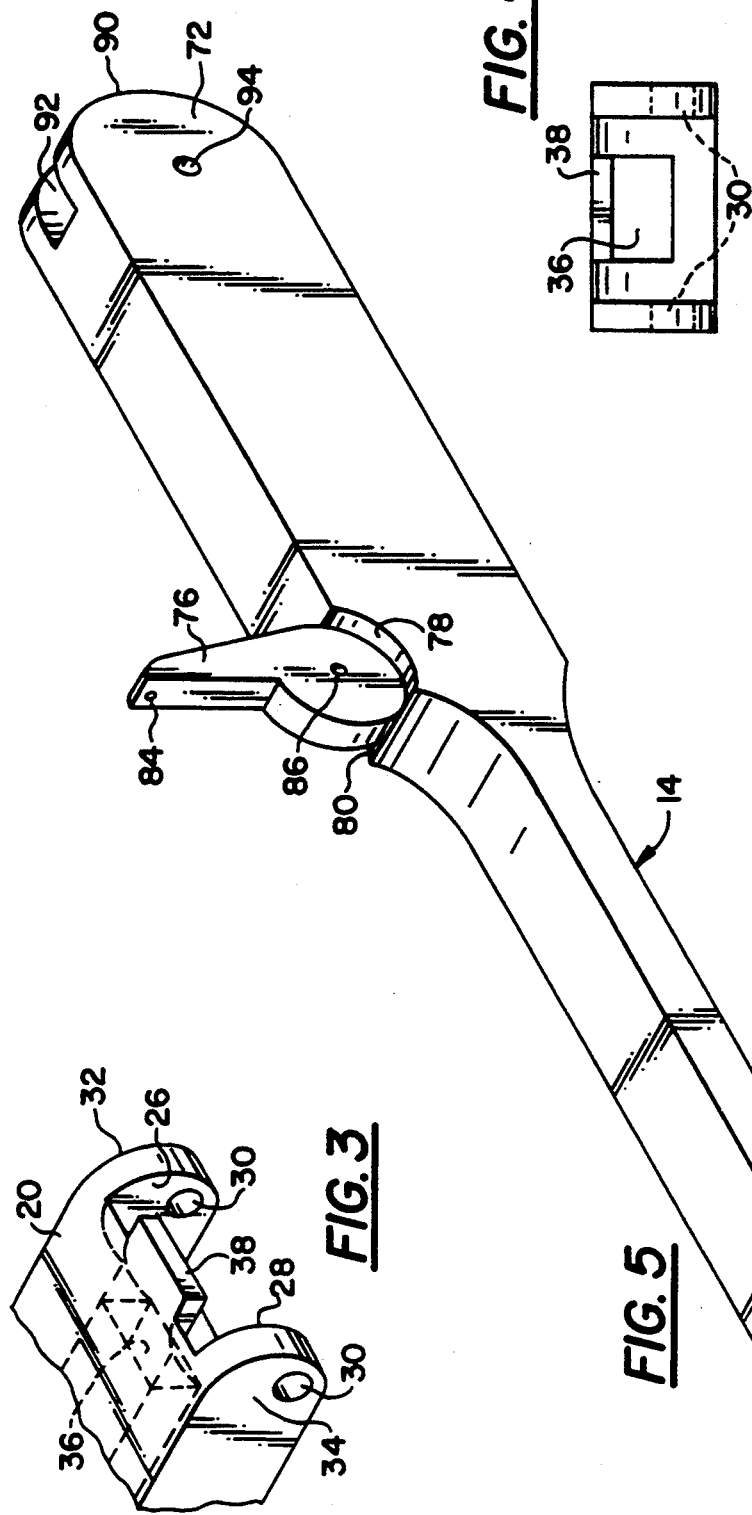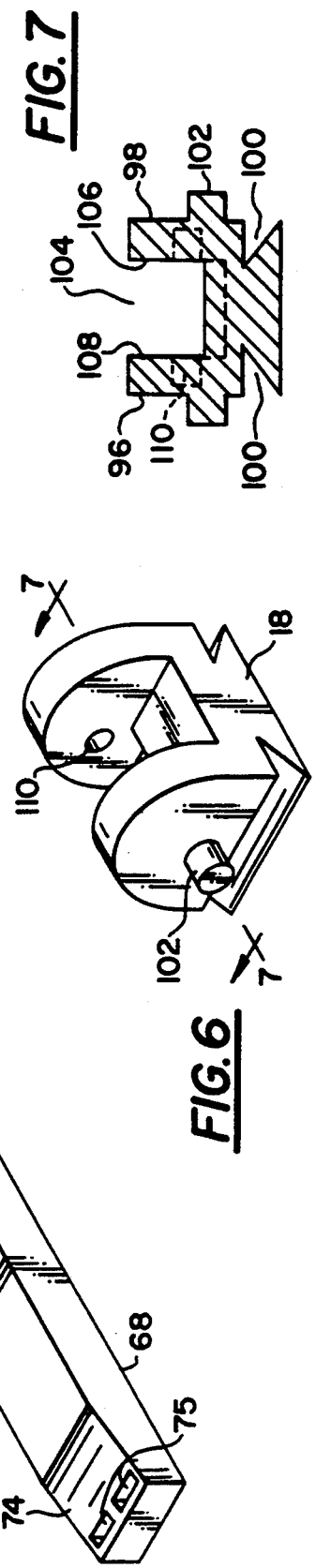

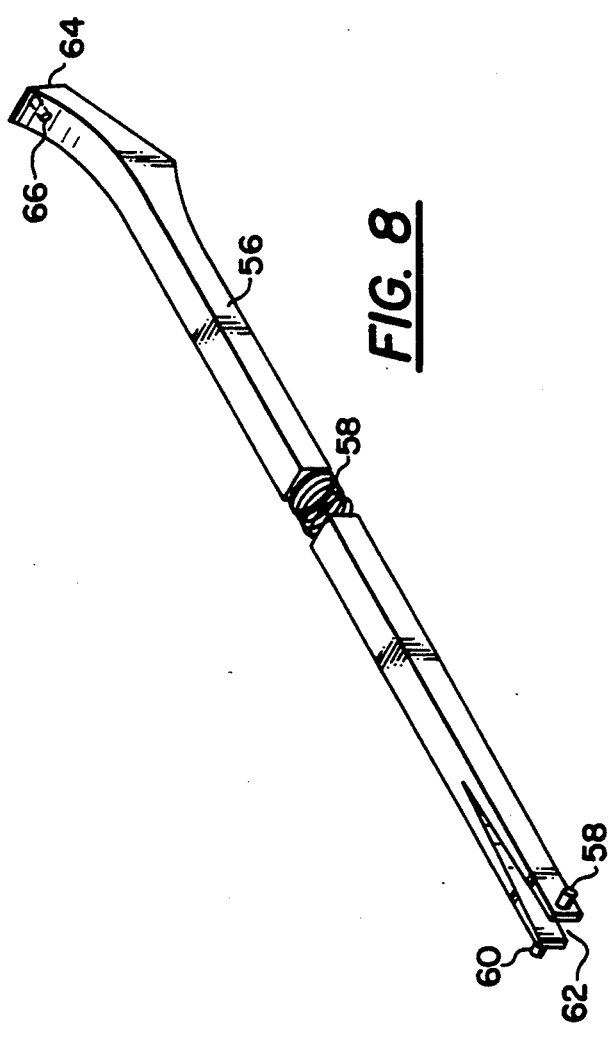
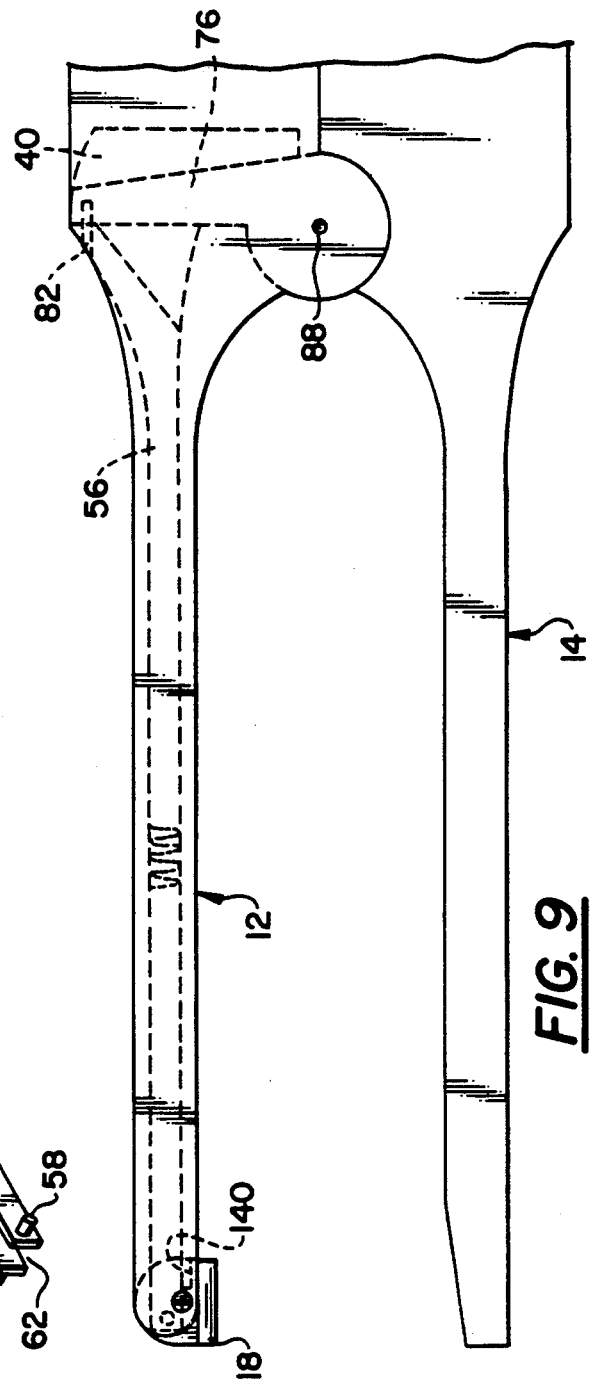

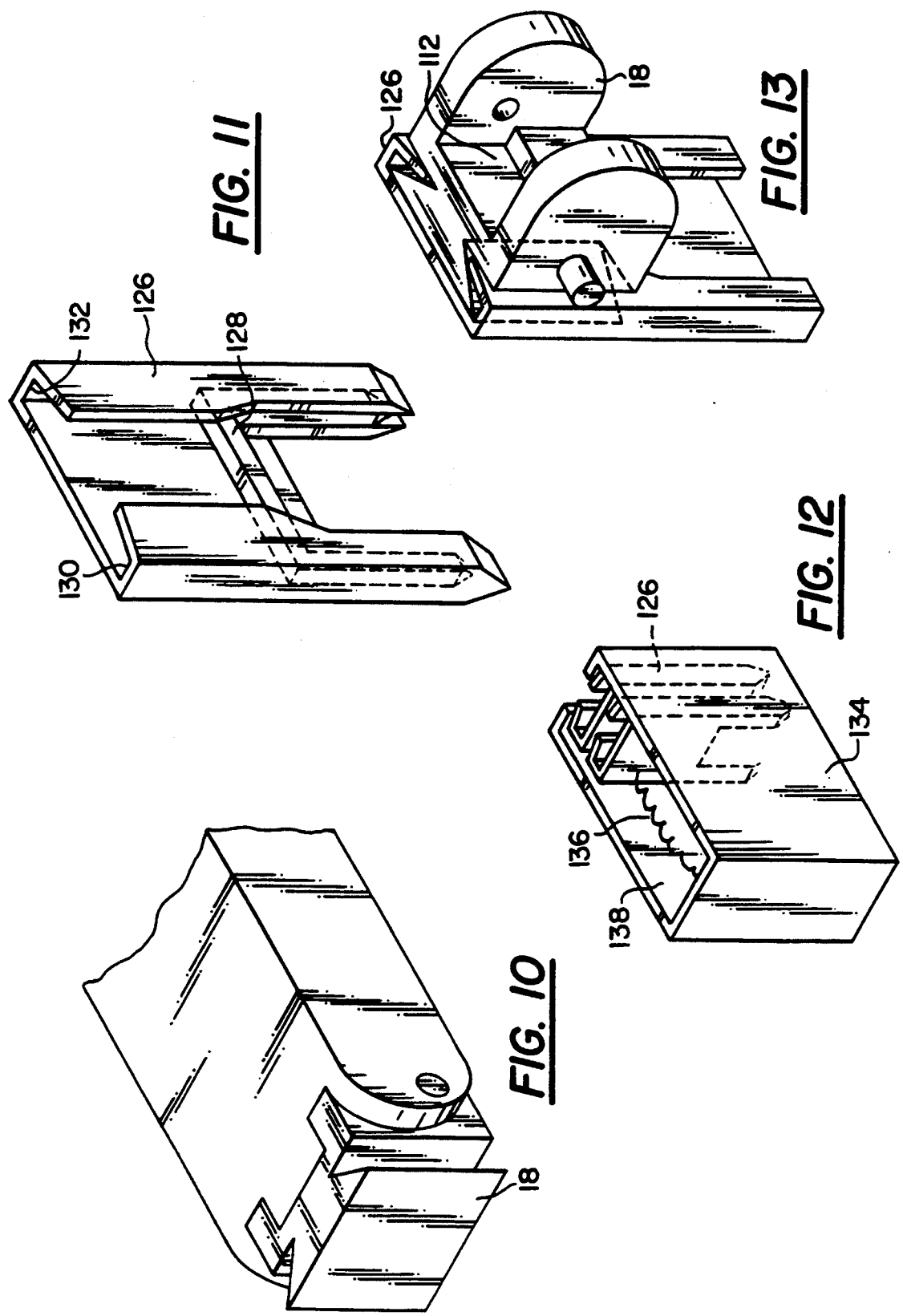

INTRANASAL SEPTAL STAPLING METHOD

This is a division of Application No. 07/858,028, filed Mar. 26, 1992, pending.

BACKGROUND OF THE INVENTION

1. Field of the Invention

This invention relates to a method and device for applying staple sutures, and more particularly to an intranasal septal stapling device for insertion into the narrow passages of the nose for dispensing staples into septal tissue.

2. Background of the Invention

Septal surgery is among the most common operations performed. It is estimated that 500,000 septal surgeries are performed each year in the United States by Otolaryngologists and Plastic Surgeons.

Septal surgery was first described in 1882, and the techniques have been modified up to the present day to correct the septum and preserve as much cartilage as possible to prevent loss of support and saddling of the external nose. Submucous resection and septoplasty are performed for nasal obstruction, sinusitis, and headache. It is often performed in conjunction with a rhinoplasty for cosmetic results.

Traditional septal surgery begins with an intranasal incision through the lining of the septum. The lining is then elevated away from the supporting skeleton by creating a tunnel on one or both sides of the septum. This allows direct visualization of the distorted bone or cartilage. Repair consists of removing or contouring the bone and cartilage. Support is assured by preserving as much cartilage as possible or by replacing crooked pieces of cartilage with straight pieces. On completion, the septum is conventionally held together with packing or suturing to prevent hematoma formation. However, intranasal packing is generally left in place 24–72 hours and causes great discomfort to the patient. Further, studies have shown that intranasal packing reduces oxygen saturation and can cause toxic shock syndrome. Therefore, intranasal packing is not a benign procedure. Unfortunately, its alternative, intranasal suturing, is technically difficult and sometimes impossible to perform.

SUMMARY OF THE INVENTION

In accordance with the present invention, intranasal stapling is employed as an adjunct or replacement of intranasal packing following submucous resection of the septum or its variation, septoplasty. Septal stapling is performed so as to support the septal tissues until healing commences. Thus, intranasal septal stapling in accordance with the invention is accomplished by passing a staple through the loose mucosa of the septum and anchoring it to the underlying septal tissue. This may mean simply joining two mucosal surfaces and allowing them to heal together as a single unit. Intranasal septal stapling may also be used in accordance with the invention to hold and secure cartilage or bone between the two mucosal membranes for added support. In the same manner, tissue grafts can be secured to the septum for repair of septal perforations.

Intranasal stapling offers two great advantages. First, the procedure is comfortable for the patient; it prevents complete nasal obstruction, thus reducing the likelihood of headaches and sinus pressure which may occur when intranasal packing is performed. Secondly, for the trained surgeon, intranasal stapling is easy and extremely quick, saving operating time.

Devices have been developed to apply staple sutures. For example, U.S. Pat. Nos. 3,575,038 and 3,278,107 disclose devices for applying staple sutures to body tissue. These devices, however, are not suitable for intranasal stapling since the stapling arms are too large to pass through the nasal cavity.

More particularly, the depth of the nasal cavity from front to back is about 7 cm in adults. The greatest depth in the nose required for stapling is 5 cm. The width of the septum varies from approximately 1 cm at the columellar entrance to 4 mm throughout the rest of the nose. The distance between the outer walls of the two nasal passages is about 2 cm at the outer nares entrance and 1.3 cm at the pyriform aperture or inner nares. The average width of each nasal passage is about 5 mm.

After a septoplasty the smallest length a staple must have is 5 mm, which allows 3 mm to penetrate the mucosal walls and 2 mm to be crimped. Since a stapler head which drives the staple must be added to the length of the staple, the 5 mm width of the nasal passage will be exceeded. Consequently, conventional stapling devices cannot be utilized for this procedure.

Thus, in accordance with a further aspect of the invention, an intranasal stapling device is provided which can be accommodated by the narrow nasal passages to perform the stapling procedure and then be easily removed. In accordance with the principles of the present invention, this object is achieved by providing a stapling device including first and second arms, each arm having a distal portion, a central portion and proximal portion; a stapler head rotatably coupled to a free end of the distal portion of the second arm. The stapler head has a first, inoperative position and a second operative position. The device includes a member for moving the stapler head from the inoperative position to the operative position, and elements for pivotly coupling the central portion of the first arm to the central portion of the second arm. The stapling device further includes first and second handle elements each pivotly coupled to each other and to the proximal portions of the first and second arms and operatively coupled to the moving member so that initial displacement of the handle elements from an inoperative position towards each other moves the distal portions of the first and second arms towards each other and actuates the moving member to move the stapler head from the inoperative position to the operative position. Further displacement of the handle elements displaces the second arm to bring the stapler head and the first arm into contact with tissue structure to be stapled. Release of the handle elements allows the moving member to return the stapler head to the inoperative position.

BRIEF DESCRIPTION OF THE DRAWINGS

FIG. 1 is a perspective view of the intranasal septal stapling device embodying the principles of the present invention;

FIG. 2 is a perspective view of the stapler arm provided in accordance with the principles of the present invention, shown with the sliding arm member removed;

FIG. 3 is an enlarged perspective view of the distal portion of the stapler arm provided in accordance with the principles of the present invention;

FIG. 4 is an enlarged front view of the distal portion of the stapler arm provided in accordance with the principles of the present invention;

FIG. 5 is a perspective view of the anvil arm provided in accordance with the principles of the present invention;

FIG. 6 is an enlarged perspective view of the stapler head provided in accordance with the principles of the present invention;

FIG. 7 is a cross-sectional view of the stapler head taken along the line 7—7 of FIG. 6;

FIG. 8 is a perspective view of the sliding arm member of the stapler arm;

FIG. 9 is a partial side elevation of the intranasal stapling device provided in accordance with the principles of the present invention;

FIG. 10 is a partial perspective view of the stapler arm with the stapler head attached and disposed in the operative position;

FIG. 11 is an enlarged perspective view of a staple capsule holding a staple, provided in accordance with the present invention;

FIG. 12 is a perspective view of a magazine for holding staple capsules provided in accordance with the principles of the present invention;

FIG. 13 is an enlarged perspective view of a staple capsule coupled to the stapler head.

DETAILED DESCRIPTION OF THE INVENTION

Figure 14:
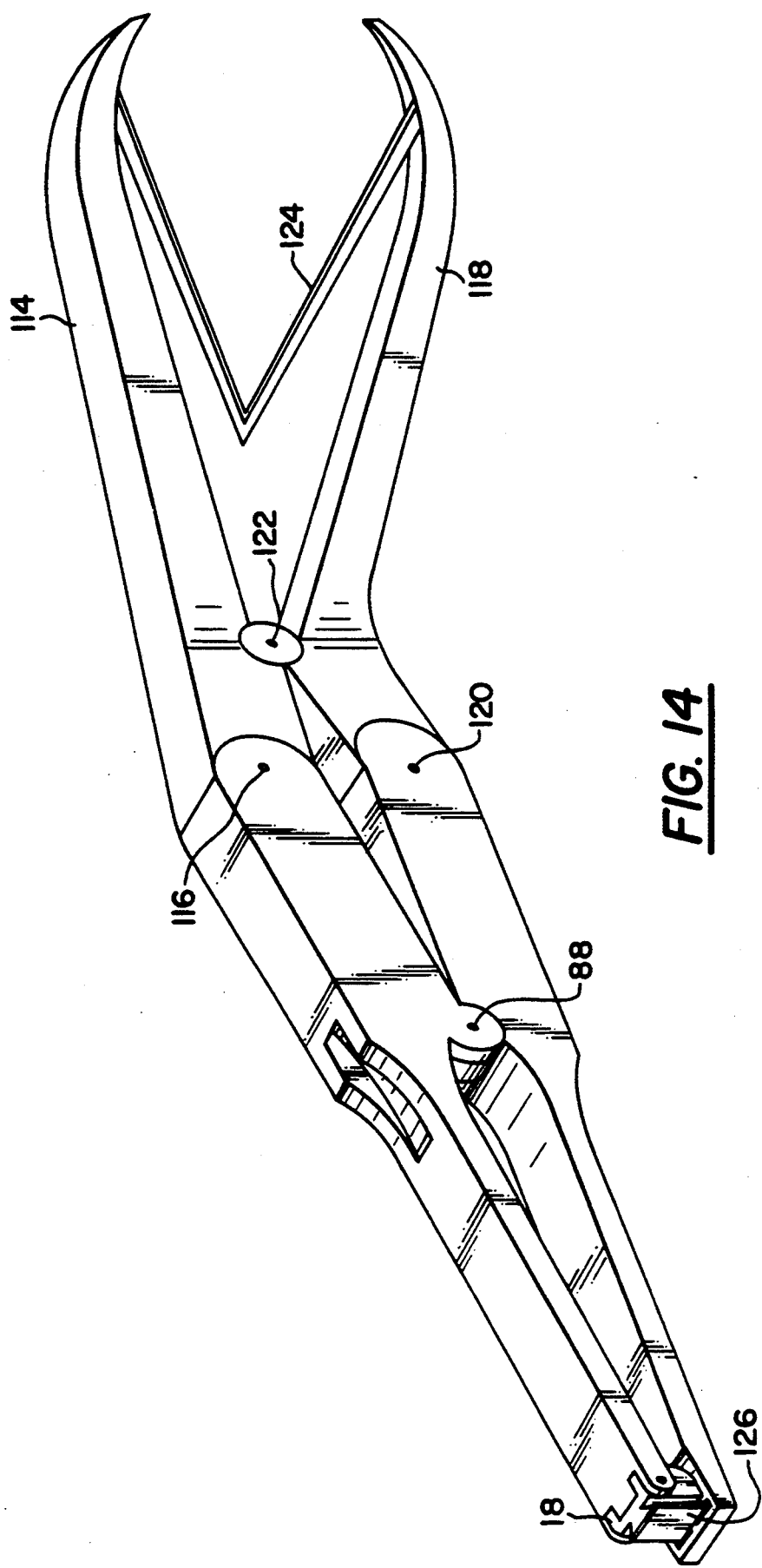
FIG. 14 is a perspective view of the intranasal septal stapling device embodying the principles of the present invention, shown in operating position.

Referring to the drawings, an intranasal septal stapling device, generally indicated at 10, which embodies the principles of the present invention, is shown.

The stapling device 10 includes a stapler arm, generally indicated at 12, an anvil arm, generally indicated at 14, a handle assembly, generally indicated at 16 and a stapler head 18.

The stapler arm 12 has a distal portion 20, a central portion 22 and a proximal portion 24, as shown in FIG. 2. The distal portion is of specific length and width so as to be capable of being inserted into a nasal passage and to extend, if necessary, along the length of the passage. The distal portion 20 is of constant width which increases at the central portion 22 for accommodating the handle assembly, which will become more apparent below. The end of the distal portion includes a slotted portion defining side walls 26, 28, as shown in FIG. 3. Each side wall 26, 28 has a bore 30 defined therethrough. The bores 30 have a common longitudinal axis which is perpendicular to the longitudinal axis of the stapler arm. The distal portion 20 has a smoothly curved outer surface so to prevent damage to the interior surfaces of the nose when inserted therein. A hollow core 36 extends the length of the distal portion and terminates at the central portion 22 of the stapler arm 12. A ledge portion 38 is defined in the end of the distal portion, the function of which will become more apparent below.

The central portion 22 of the stapler arm 12 includes a cutout portion 40 extending in a direction perpendicular to the longitudinal axis of the stapler arm. Below the cutout portion, two leg members 44 define a channel 46. A bore 48 is disposed perpendicular to the longitudinal axis of the stapler arm and extends through each leg member 44.

End 50 of the proximal portion 24 of the stapler arm has a curved outer periphery. End 50 includes a slot 52 disposed along the longitudinal axis of the stapler arm. A bore 54 is defined perpendicular to the longitudinal axis of the stapler arm at end 50. The slot 52 and bore 54 are used to pivotly couple a portion of the handle assembly 16 to the stapler arm.

The stapler arm 12 further includes an elongated sliding arm member 56 (FIG. 8) which is slidably disposed in hollow bore 36, which extends along the entire length of the distal portion 20. The sliding arm member 56 is divided by a high tension spring 58, the function of which will be described below. The distal tip of the sliding arm member 56 includes two lateral projections 58, 60 which function as pivot pins for rotation, once mated with the stapler head 18. In the illustrative embodiment, the lateral projections 58, 60 are divided by a V-shaped cutout 62 which allows the projections to resiliently spring toward each other during assembly, as discussed below. As an alternative, each projection may be spring loaded to provide the same function, or the pivot coupling can be defined by a pin which extends though bores in arm member 56 and stapler head 18. The proximal end of the sliding arm member 56 inclines gradually upward and terminates at planar surface 64. Planar surface 64 includes a bore 66 for receiving a screw or the like, as described below.

The stapling device 10 includes a stapler head 18. As shown in FIGS. 6 and 7, the stapler head 18 includes side surfaces 96 and 98 having curved outer peripheral surfaces so that no tissue is damaged when the device is inserted into or removed from the nasal passage. A V-shaped groove 100 is defined in distal end of each side surface 96, 98. Side surfaces 96 and 98 each have a cylindrical protrusion 102 centrally disposed thereon, about a common axis. A channel 104 is formed through the stapler head between the side surfaces so to define interior surfaces 106, 108. Each interior surface 106, 108 includes a blind hole 110. A recess is formed in the channel 104 defining surface 112, the function of which will become more apparent below.

The lateral projections 58, 60 of the sliding arm member 56 are sprung together by utilizing the V-shaped cutout 62 and inserted into the blind holes 110 in the stapler head 18. The lateral projections spring back to their natural position so as to couple the sliding arm member to the stapler head, permitting the stapler head to rotate with respect to the sliding arm member. Protrusions 102 are fitted with bores 30 in the stapler arm 12, so that the stapler head 18 can rotate with respect to the stapler arm. The stapler head is now fully assembled with the stapler arm.

The anvil arm 14, as shown in FIG. 5, includes a distal portion 68, a central portion 70 and proximal portion 72. Like the stapler arm, the distal portion 68 is of specific length and width so as to be insertable into and capable of extending along a nasal passage. The distal portion 68 is of constant width and extends to the central portion 70, where the width of the anvil arm increases to facilitate coupling to the handle assembly. The end of the distal portion 68 of the anvil arm 14 contains an angled anvil 74. Two indentations 75 are defined in the angled anvil which are used to bind and close the staple legs during stapling.

The proximal portion 72 of the anvil arm includes a lever 76 extending vertically upward from the longitudinal axis of the anvil arm 14. Curved recesses 78, 80 are defined on each side of the lever 76 for accepting leg members 44 of the stapler arm 12. The lever 76, is inserted into cutout 40 of the stapler arm when the device is in operating condition, as shown in FIG. 9. A screw or the like 82 is disposed through bore 66 of the sliding arm member into a threaded hole 84 of the lever so as to couple the lever to the sliding arm member. A bore 86 equal in size to bore 48 of the stapler arm, is disposed through the lower portion of the lever 76. A pin 88 is disposed through bores 86 and 48 so to pivotly couple the anvil arm to the stapler arm.

End 90 of the proximal portion 72 of the anvil arm has a curved outer periphery. End 90 includes an slot 92. A bore 94 is disposed at end 90 perpendicular to the longitudinal axis of the anvil arm. The slot 92 and bore 94 are used to pivotly couple the handle assembly 16 to the anvil arm, the function of which will become more apparent below.

The intranasal stapling device 10 includes a handle assembly, generally indicated at 16, shown in FIGS. 1 and 14. The handle assembly includes an upper handle member 114 having a slot (not shown) to mate with the slot 52 of the stapler arm. The upper handle member is pivotly coupled to the stapler arm 12 by pin 116. The handle assembly also includes a lower handle member 118. The lower handle member also includes a slot (not shown) to mate with slot 92 of the anvil arm 14. The lower handle member 118 is pivotly coupled to the anvil arm by pin 120. In addition, the lower and upper handle members are pivotly connected by pin 122. A spring 124 is disposed between the upper handle member and lower handle member and is affixed to each end thereof allowing the handle members to be resilient.

The device 10 is further provided with staple capsules 126, one of which is shown in FIG. 11. Each capsule houses a staple 128. The staples are preferably made of bio-absorbable material and thus, need not be removed once inserted into the nasal tissue. Each capsule 126 includes interior surfaces 130, 132, which function as a guide rail for the staple for directing the staple out of the capsule, upon stapling. The capsule has both ends open with one open side wall. The staple capsules are arranged in a row in a magazine 134 as shown in FIG. 12, and are biased against one side of the magazine by spring 136. The magazine 134 has an opening 138 in the top thereof to enable easy withdrawal of the capsule. The axial length of each capsule 126 is about 4 mm greater than the height of the staples to accommodate the stapler head.

With reference to the Figures, the operation of the intranasal stapling device 10 of the present invention can be appreciated. FIG. 1 shows the stapler device in a normally biased position. The stapler arm 12 and anvil arm 14 are initially in a parallel relation when the device 10 is in the normally biased position. While in the normally biased position, the stapler head 18 is in a low profile, inoperable position with the longitudinal axis of the capsule and the longitudinal axis of the stapler arm in a parallel relation.

The foremost staple capsule 126 in magazine 134 is removed therefrom and coupled to the stapler head 18. The dove-tail head of the stapler head 18 engages with the groove of the capsule frictionally holding the capsule to the stapler head. The capsule housing the staple is then moved to the entrance of one nostril with the anvil arm being aligned with the other nostril.

The stapler arm 12 with the stapler head in the low profile position, and anvil arm 14 are introduced into the nose to the desired location. In this low profile position, surface 112 of the stapler head 18 abuts a bottom surface 140 of the stapler arm 12, preventing the stapler head from rotating during insertion. The upper and lower handle members are then manually shifted slightly toward each other. As shown in FIG. 14, this slight actuation moves the distal portion of the anvil arm toward the distal portion of the stapler arm due to the device 10 pivoting about pins 122 and 88 causing pins 116 and 120 to move away from each other. The lever 76 of the anvil arm 14 will rotate about pin 88 approximately 10 degrees within the cutout 40 of the stapler arm, which moves the sliding arm member 56 in the hollow core 36, towards the proximal portion of the stapler arm. Thus, the rotational motion of the lever 76 causes the sliding arm member to move linearly within the stapler arm.

Since the stapler head 18 is rotatably coupled to the sliding arm member 56, the stapler head will rotate about protrusions 102 mating with the distal end of the stapler arm, moving the capsule to an operative position, perpendicular to the longitudinal axis of the stapler arm. In this position, surface 112 of the stapler head 18 abuts ledge 38 of the stapler arm 12, to prevent rotation of the stapler head beyond 90 degrees, as shown in FIG. 10 (capsule omitted for clarity). The rotation of the stapler head is preferably accomplished inside the nose and is possible because the septum is flexible after surgery. Once the stapler head is rotated to its operative position, so that the capsule is perpendicularly aligned with the anvil arm, the upper and lower handle members 114, 118, are brought closer together. The high tension spring 58 of the sliding arm member 56 allows further displacement of the handle inspite of the prior complete shifting of the head 18 and thus prevents the stapler head 18 from locking and binding. This second action of the handle members brings the staple capsule 126 and anvil arm 12 toward one another. Because further motion of the capsule is restricted by the septal tissue, further actuation of the handle causes the stapler head to force the staple out of the capsule and through the nasal tissue. In the event the staple extends all the way through the septum, the staple will be bent against the anvil. The stapler head moves down into the capsule, taking the previous position of the staple. The handle members are then released, which permits the lever 76 to rotate back to its original position, prior to stapling, which in turn shifts the capsule and stapler head to rotate back to the low profile position and be withdrawn. The capsule remains on the stapler head until it is manually removed.

It can be appreciated that the intranasal stapling device 10 of the present invention permits relatively large bio-absorbable staples to be delivered through a small entrance (the nares), down a narrow passageway to the eventual destination deep within the nose. For increased accuracy, a nasal speculum may be employed which allows direct visualization of the stapling procedure. If cartilage is to be replaced, pockets for insertion of the cartilage can be created by stapling. In addition, tears in the mucosa can be repaired with staples, and soft tissue grafts for perforation can be accurately anchored with stapling.

While the invention has been described in connection with what is presently considered to be the most practical and preferred embodiment, it is to be understood that the invention is not limited to the disclosed embodiment, but, on the contrary, is intended to cover various modifications and equivalent arrangements included within the spirit and scope of the appended claims. For example, although a method and device for intranasal septal stapling has been described, the device of the invention could be used for stapling other structures during other surgical procedures as well.

What is claimed is:

1. A method of securing nasal tissue comprising the steps of:

providing a staple driving device including at least one arm member sized and configured to be inserted into a nasal passage;

inserting said at least one arm member into a nasal passage;

driving a staple at least partially through the nasal tissue with said at least one arm member; and withdrawing said at least one arm member from the nasal passage leaving the staple in securement with the nasal tissue.

2. The method according to claim 1, wherein said step of driving a staple includes driving a staple formed from bio-absorbable material.

3. The method according to claim 1, wherein the nasal tissue is septal tissue.

4. The method according to claim 3, wherein said step of driving a staple is preceded by submucous resection of the septum, said nasal tissue being septal tissue.

* * * * *